(12) United States Patent
Christiansen et al.

(10) Patent No.: US 9,000,220 B2
(45) Date of Patent: Apr. 7, 2015

(54) ORGANOPHOSPHORUS COMPOUNDS BASED ON TETRAPHENOL (TP)-SUBSTITUTED STRUCTURES

(75) Inventors: Andrea Christiansen, Neu-Ulm (DE); Robert Franke, Marl (DE); Dirk Fridag, Haltern am See (DE); Dieter Hess, Marl (DE); Burkard Kreidler, Recklinghausen (DE); Dieter Vogt, Nuenen (NL); Laura Bini, Maastricht (NL); Michele Janssen, Eindhoven (NL); Bart Hamers, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 20 days.

(21) Appl. No.: 13/393,109

(22) PCT Filed: Aug. 26, 2010

(86) PCT No.: PCT/EP2010/062466
§ 371 (c)(1),
(2), (4) Date: Apr. 18, 2012

(87) PCT Pub. No.: WO2011/023756
PCT Pub. Date: Mar. 3, 2011

(65) Prior Publication Data
US 2012/0197025 A1 Aug. 2, 2012

(30) Foreign Application Priority Data

Aug. 31, 2009 (DE) .......................... 10 2009 029 050

(51) Int. Cl.
| | | |
|---|---|---|
| *C07F 9/145* | (2006.01) | |
| *C07D 213/30* | (2006.01) | |
| *C07F 9/655* | (2006.01) | |
| *C07C 37/20* | (2006.01) | |
| *C07C 39/15* | (2006.01) | |
| *C07C 45/50* | (2006.01) | |
| *C07C 67/303* | (2006.01) | |
| *C07C 209/26* | (2006.01) | |
| *C07C 253/10* | (2006.01) | |
| *C07D 333/16* | (2006.01) | |
| *C07F 9/6571* | (2006.01) | |
| *C07F 9/6574* | (2006.01) | |
| *C07F 9/6584* | (2006.01) | |
| *C07F 15/04* | (2006.01) | |

(52) U.S. Cl.
CPC .......... *C07D 213/30* (2013.01); *C07F 9/65522* (2013.01); *C07C 37/20* (2013.01); *C07C 39/15* (2013.01); *C07C 45/50* (2013.01); *C07C 67/303* (2013.01); *C07C 209/26* (2013.01); *C07C 253/10* (2013.01); *C07D 333/16* (2013.01); *C07F 9/145* (2013.01); *C07F 9/657154* (2013.01); *C07F 9/65746* (2013.01); *C07F 9/65848* (2013.01); *C07F 15/04* (2013.01); *C07F 15/045* (2013.01)

(58) Field of Classification Search
USPC ........................................................ 568/12
See application file for complete search history.

(56) References Cited

U.S. PATENT DOCUMENTS

| | | | |
|---|---|---|---|
| 3,309,337 | A | 3/1967 | Hurlock et al. |
| 3,836,590 | A | 9/1974 | Brindell et al. |
| 4,001,183 | A | 1/1977 | Freitag et al. |
| 5,012,016 | A | 4/1991 | Li |
| 5,191,128 | A | 3/1993 | Li |
| 5,863,992 | A | 1/1999 | McCloskey et al. |
| 6,570,033 | B2 | 5/2003 | Röttger et al. |
| 6,818,770 | B2 | 11/2004 | Selent et al. |
| 7,009,068 | B2 | 3/2006 | Schmutzler et al. |
| 7,161,020 | B2 | 1/2007 | Selent et al. |
| 7,193,116 | B2 | 3/2007 | Moeller et al. |
| 7,317,130 | B2 | 1/2008 | Möller et al. |
| 7,345,185 | B2 | 3/2008 | Ortmann et al. |
| 7,495,133 | B2 | 2/2009 | Borgmann et al. |
| 7,495,134 | B2 | 2/2009 | Hess et al. |
| 7,589,081 | B2 | 9/2009 | Zapf et al. |
| 7,767,861 | B2 | 8/2010 | Ortmann et al. |
| 8,003,816 | B2 | 8/2011 | Selent et al. |
| 8,226,829 | B2 | 7/2012 | Wiese et al. |

(Continued)

FOREIGN PATENT DOCUMENTS

| | | |
|---|---|---|
| EP | 0 819 718 | 1/1998 |
| EP | 1 191 018 | 3/2002 |

(Continued)

OTHER PUBLICATIONS

Van Den Beuken, E.K., et al., "Synthesis and crystal structure of a dinuclear rhodium complex, Catalytic activity of mono-and di-nuclear rhodium phosphite complexes in hydroformylation," Journal of the Chemical Society Dalton Trans., No. 17, pp. 3561-3569, (1996).

Bini, L., "Mechanistic Insights into the Hydrocyanation Reaction," NIOK, Total 2 Pages, (Jun. 30, 2009).

Gruettner, C., et al., "A Convenient and General Synthesis of Alkanediyl Diphenols," Journal of the Chemical Society, Perkin Transactions 1, pp. 93-94, (Jan. 1, 1995).

Reetz, M.T., et al., "New Diphosphite Ligands for Catalytic Asymmetric Hydrogenation: The Crucial Role of Conformationally Enantiomeric Diols," Angew. Chem. Int. Ed., vol. 38, No. 1/2, pp. 179-181. (1999).

(Continued)

*Primary Examiner* — Shawquia Jackson
(74) *Attorney, Agent, or Firm* — Oblon, McClelland, Maier & Neustadt, L.L.P.

(57) ABSTRACT

The invention relates to the synthesis of tetraphenol-substituted structures, in particular meta-substituted xylenes. Said tetraphenol-type structures are reacted to obtain organic phosphorus compounds, in particular organophosphites. The invention further relates to the production of catalytically active compositions which contain transition metals in addition to the aforementioned organic phosphorus compounds. According to another subject matter of the invention, said catalytically active compositions are used in chemical reactions with small molecules, e.g. HCN, CO, hydrogen, and amines.

12 Claims, No Drawings

(56) References Cited

U.S. PATENT DOCUMENTS

| | | |
|---|---|---|
| 2006/0052624 A1 | 3/2006 | Galland et al. |
| 2009/0292146 A1 | 11/2009 | Hess et al. |
| 2010/0137623 A1 | 6/2010 | Selent et al. |
| 2010/0197873 A1 | 8/2010 | Wasserman et al. |
| 2011/0130595 A1 | 6/2011 | Lueken et al. |
| 2013/0030233 A1 | 1/2013 | Boeing et al. |

FOREIGN PATENT DOCUMENTS

| | | |
|---|---|---|
| GB | 942 594 | 11/1963 |
| GB | 1 333 812 | 10/1973 |
| JP | 61 270189 | 11/1986 |
| JP | 2 252724 | 10/1990 |
| JP | 3 36087 | 2/1991 |
| WO | 2008 134118 | 11/2008 |

OTHER PUBLICATIONS

Maslennikova, V.I., et al., "Regiodirected phosphorylation of 2,2',7,7'—tetrahydroxydinaphthylmethane," Tetrahedron, vol. 63, pp. 4162-4171, (2007).

Janssen, M., et al., "Tetraphenol-based diphosphite ligands: synthesis, characterization, and application in the rhodium-catalyzed hydroformylation of octenes," Tetrahedron Letters, vol. 51, pp. 1971-1975, (2010).

Bini, L., et al., "Mechanistic insights into the hydrocyanation reaction/door," Eindhoven: Technische Universiteit Eindhoven, Total 3 Pages, (2009).

Bini, L., "Hydrocyanation of 3-Pentenenitrile with Tetraphenol-Based Diphosphite Ligands: Formation of $\pi$-Allyl and $\alpha$-Alkyl Intermediates," Chapter 4, pp. 101-120, (Sep. 10, 2009).

International Search Report Issued Apr. 8, 2011 in PCT/EP10/62446 Filed Aug. 26, 2010.

U.S. Appl. No. 13/582,265, filed Aug. 31, 2012, Christiansen, et al.
U.S. Appl. No. 13/822,650, filed Mar. 13, 2013, Franke, et al.
U.S. Appl. No. 14/357,090, filed May 8, 2014, Christiansen, et al.

ORGANOPHOSPHORUS COMPOUNDS BASED ON TETRAPHENOL (TP)-SUBSTITUTED STRUCTURES

The present invention relates to novel organic compounds, their phosphorus derivatives, i.e., organic phosphorus compounds, and to complexed compounds thereof with transition metals, processes for their production and use in catalytic reactions.

The reactions between olefin compounds, carbon monoxide and hydrogen in the presence of a catalyst to form the aldehydes having one carbon atom more is known as hydroformylation (oxo synthesis). Catalysts used in these reactions are frequently compounds of the transition metals of groups 8 to 10 of the periodic table, especially compounds of rhodium and of cobalt. Hydroformylation using rhodium compounds generally offers the advantage of higher selectivity compared with catalysis using cobalt compounds and hence is usually more economical. Rhodium-catalyzed hydroformylation usually employs complexes consisting of rhodium and preferably of trivalent phosphorus compounds as ligands. Known ligands are for example compounds from the classes of phosphines, phosphites and phosphonites. Hydroformylation of olefins is reviewed in B. CORNILS, W. A. HERRMANN, "Applied Homogeneous Catalysis with Organometallic Compounds", Vol. 1&2, VCH, Weinheim, N.Y., 1996.

Each catalyst system (cobalt or rhodium) has its specific merits. Different catalyst systems are used depending on the feedstock and the target product. With rhodium and triphenylphosphine, α-olefins can be hydroformylated at comparatively low pressures. Triphenyl-phosphine as phosphorus-containing ligand is generally used in excess, while a high ligand/rhodium ratio is required to increase the selectivity of the reaction leading to the commercially desired n-aldehyde product.

U.S. Pat. Nos. 4,694,109 and 4,879,416 concern bisphosphine ligands and their use in the hydroformylation of olefins at low syngas pressures. Ligands of this type do provide high activities and high n/i selectivities in the hydroformylation of propene in particular.

WO-A-95/30680 describes bidentate phosphine ligands and their use in catalysis including inter alia in hydroformylation reactions.

Ferrocene-bridged bisphosphines are disclosed for example in U.S. Pat. Nos. 4,169,861, 4,201,714 and 4,193,943 as ligands for hydroformylations.

The disadvantage of bidentate phosphine ligands is their relatively costly method of making. Therefore, it is often not economically viable to use such systems in commercial processes.

Rhodium-monophosphite complexes are suitable catalysts for the hydroformylation of branched olefins having internal double bonds, but the selectivity for terminally hydroformylated compounds is low.

EP-A-0 155 508 discloses the use of bisarylene-substituted monophosphites in rhodium-catalyzed hydroformylation of sterically hindered olefins, for example isobutene.

Rhodium-bisphosphite complexes catalyze the hydroformylation of linear olefins having terminal and internal double bonds to give predominantly terminally hydroformylated products, whereas branched olefins having internal double bonds are only converted to a minor extent. These phosphites do coordinate onto a transition metal center to provide catalysts of enhanced activity, but the on-stream life of these catalyst systems is unsatisfactory, inter alia because of the phosphite ligands' sensitivity to hydrolysis. The use of substituted bisaryl diols as starting materials for the phosphite ligands, as described in EP-A-0 214 622 or EP-A-0 472 071, wrought appreciable improvements.

The literature says that the rhodium complexes of these ligands are extremely active hydroformylation catalysts for a α olefins. U.S. Pat. Nos. 4,668,651, 4,748,261 and 4,885,401 describe polyphosphite ligands whereby α-olefins but also 2-butene can be converted to the terminally hydroformylated products with high selectivity. U.S. Pat. No. 5,312,996 also uses bidentate ligands of this type for hydroformylating butadiene.

Tetraphenols are known from the field of light-sensitive, film-forming materials (photoresists). Representatives of tetraphenols are described in JP 05034915 and JP 2004277358. Journal of the Chemical Society, Perkin Transactions 1: Organic and Bio-Organic Chemistry (1972-1999) (1994), (13), 1879-82 and JP 2004277358 point up pathways to preparing the precursors needed as well as to the tetraphenol compounds.

Macromolecules (Washington, D.C., United States) (2008), 41(20), 7306-7315 describes for example the use of tetraphenol compounds in the ring-opening polymerization of ethylene oxide and propylene oxide.

Although the aforementioned bisphosphites are good complexing ligands for rhodium-based hydroformylation catalyst systems, it is desirable to develop novel easily obtainable phosphites to further improve their efficacy in hydroformylation for example.

It is an object of the present invention to prepare organic compounds which, in terms of their structure, can be categorized as tetraphenols, and convert them into their phosphorus derivatives.

It is also an object in this connection for the method of preparing the organic compounds as well as the organic phosphorus compounds derived therefrom to be technically and economically undemanding. The focus in this connection is on a modular construction of the organic phosphorus compounds in order that varied structures may be generated in a few steps and also that starting materials conveniently available on a large industrial scale may be used for this.

These phosphorus derivatives, or the organic phosphorus compounds mentioned at the beginning, are further processed with transition metals to form catalytically active compositions. It is further an object to employ these catalytically active compositions in reactions of small molecules, for example CO, HCN, hydrogen or else amines, in pure form as well as mixed, with unsaturated hydrocarbon compounds. It is also an object that these catalytically active compositions used in the hydroformylation of unsaturated hydrocarbon compounds, for example, have a long on-stream life and hence the organic phosphorus compounds used as ligands have a low sensitivity to hydrolysis as well as a high selectivity to the linear, i.e. n-hydroformylated, product.

The invention provides organic compounds of formula 1

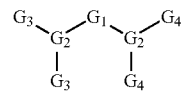

where:
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 and G4 are the same or different, are each substituted by an OH group and are each an at least disubstituted cyclic structure selected from the group of aromatics, heteroaromatics, fused aromatics systems or fused heteroaromatic systems with any desired further substitution, and connected to G2 by a monovalent bond in each case.

In a preferable embodiment, the variety of possible structures derivable from formula 1 reduces as a result of the following restrictions being introduced, viz.:

G1 is an at least disubstituted 1,2-, 1,3- or 1,4-phenyl radical;

G2 is a C1-alkyl radical with tertiary or quaternary substitution;

G3 and G4 are the same and are each an at least disubstituted aromatic radical having one OH group in each case and selected from the group of aromatics, heteroaromatics, fused aromatics systems or fused heteroaromatic systems with any desired further substitution. Exemplary of this preferable embodiment are the following structures wherein G1 has a 1,3-substitution:

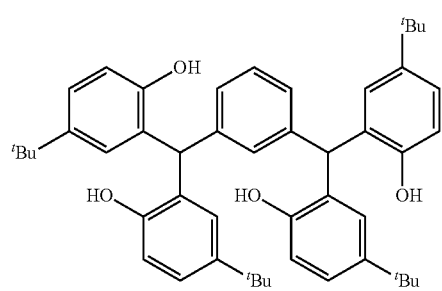

11

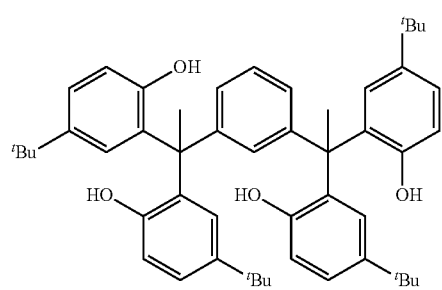

12

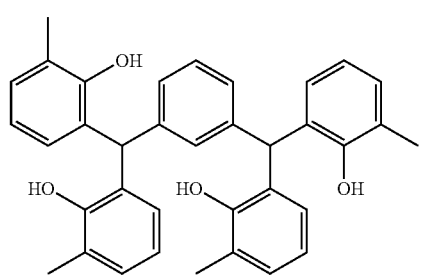

13

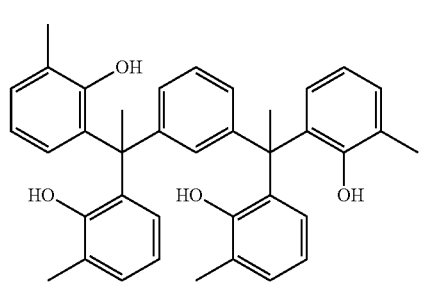

14

-continued

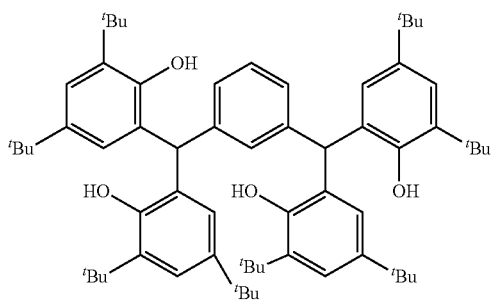

15

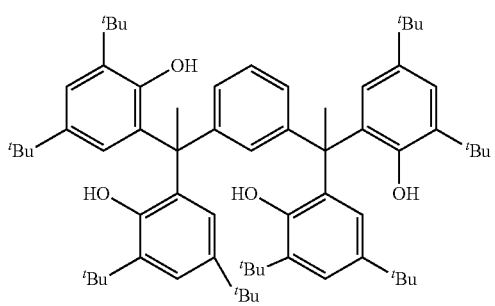

16

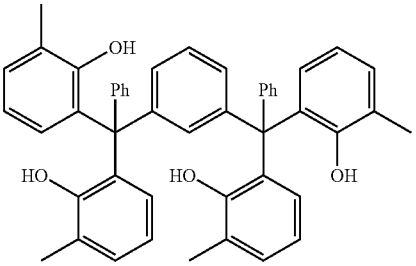

17

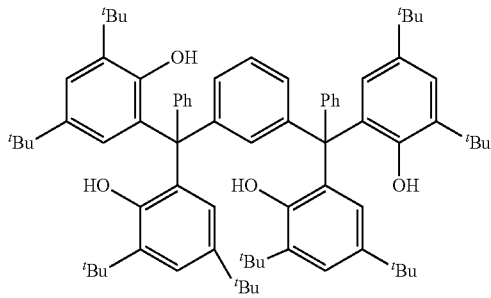

18

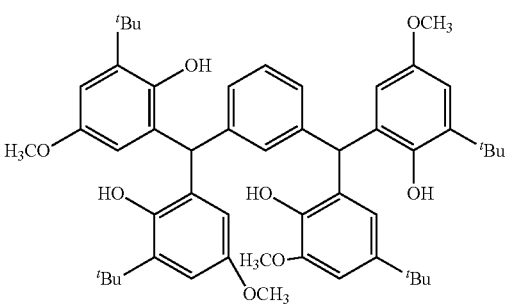

19

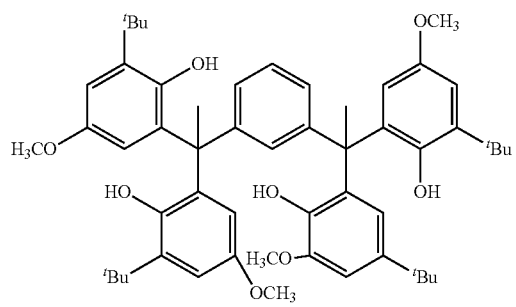
20
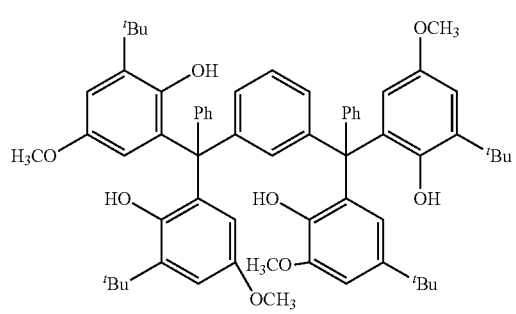
21
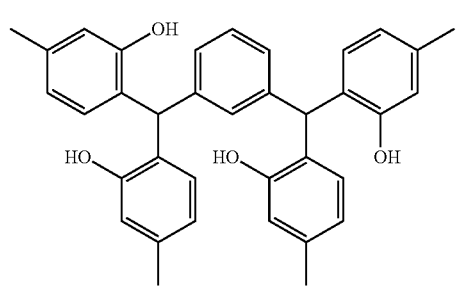
22
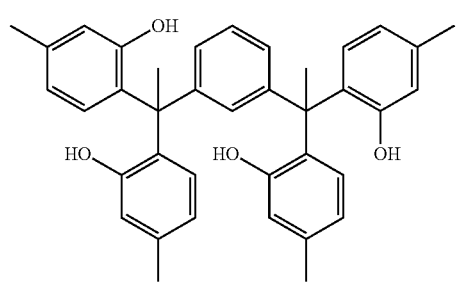
23
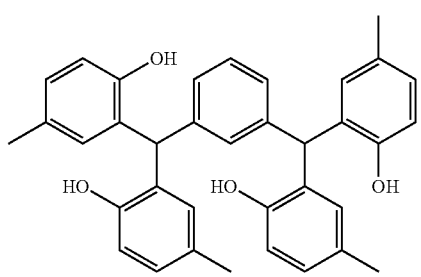
24
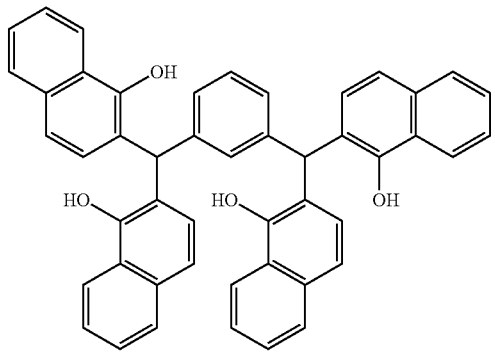
25
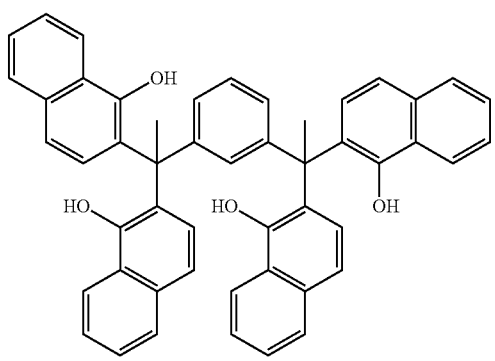
26
Exemplary of this preferable embodiment is also for example:
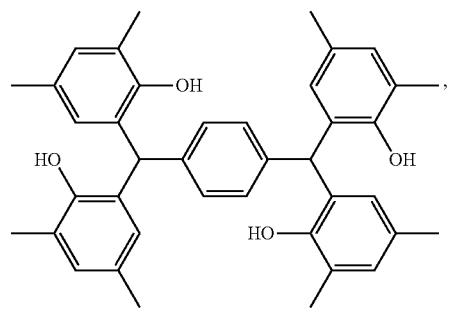
27
where G1 has a 1 4-substitution, while the following execution of formula 28 depicts, by way of example, a representative wherein G1 shows a 1,2-substitution:
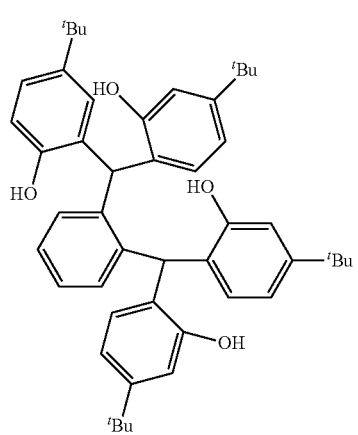
28

Exemplary representatives of this embodiment further include the following derivatives of formulae 29 to 38 which feature for G1 a trisubstitution, a heteroaromatic or a fused aromatic system:
29
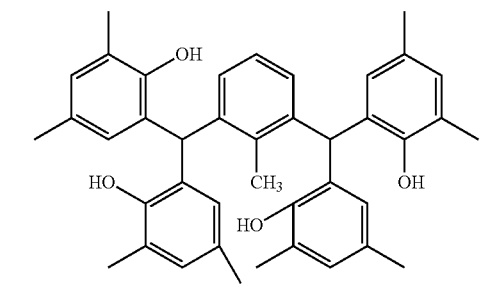
30
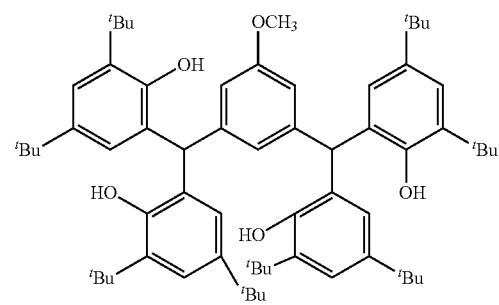
31
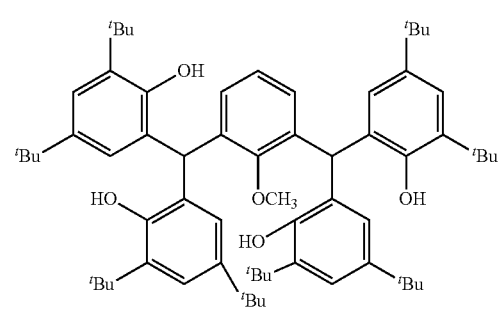
32
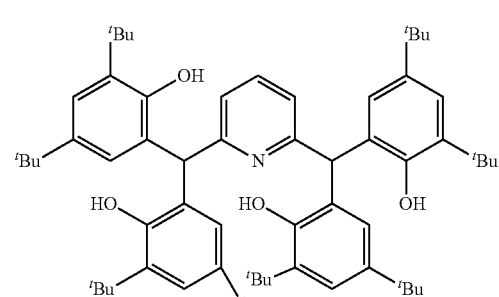
33
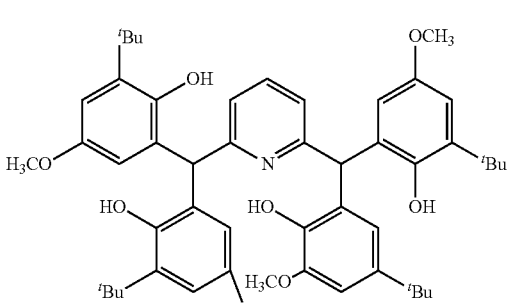
34
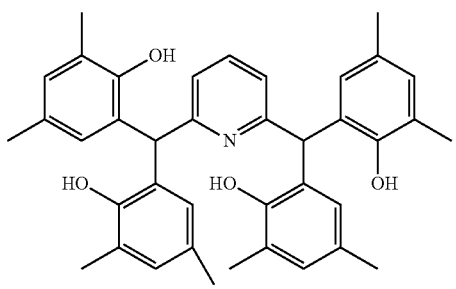
35
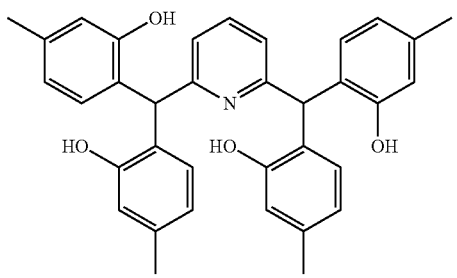
36
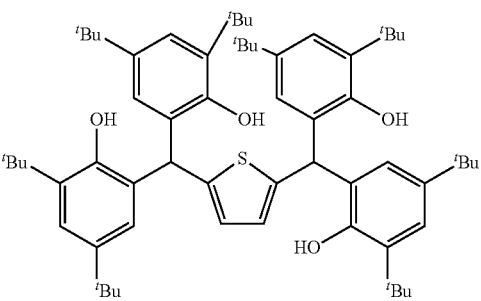
37
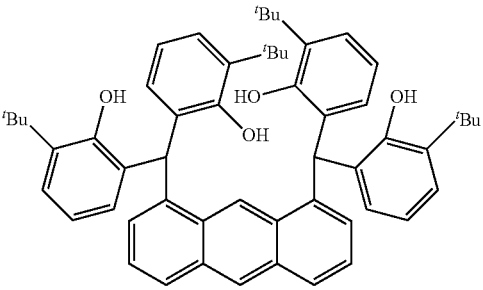
38
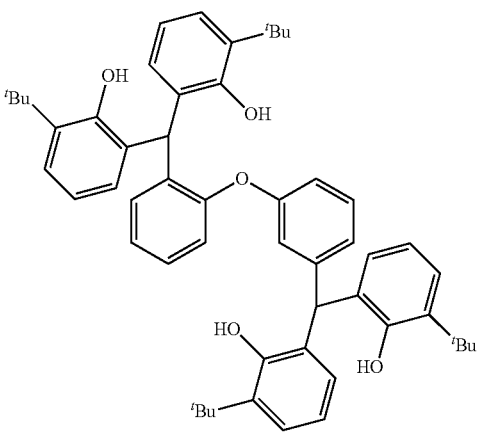
In a further preferable embodiment according to formula 1:
G1 is an at least disubstituted 1,3-phenyl radical;

G2 is a C1-alkyl radical substituted with hydrogen, methyl, ethyl, isopropyl, isobutyl, trifluoromethyl or aryl;

G3 and G4 are the same and are each an at least disubstituted aromatic radical provided with OH, C1 to C6 O-alkyl and also C1 to C6-alkyl.

Exemplary representatives of this embodiment are reproduced in formulae 11 to 26 and also 29 to 31 for example. They are prepared as hereinbelow disclosed in the preparation examples according to the invention.

In another preferable embodiment according to formula 1:
G1 is a 1,3-disubstituted phenyl radical;
G2 is a C1-alkyl radical substituted with hydrogen, methyl, ethyl, isopropyl, isobutyl, trifluoromethyl or aryl;
G3 and G4 are the same and an aromatic radical trisubstituted with OH and also 2 tert-butyl groups.

Claimed representatives of this embodiment are disclosed for example in formulae 12, 15, 16 and 18 and are synthesizable on the basis of preparation examples according to the invention. In the preparation examples according to the invention, the claimed representatives are designated as TP0, TP'0 and TP"0 for clarity.

The invention further provides organic phosphorus compounds of formula 2:

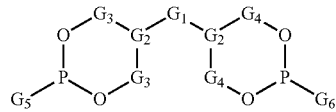

2 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 and G4 are the same or different and are each an at least monosubstituted cyclic structure selected from the group of aromatics, heteroaromatics, fused aromatics systems or fused heteroaromatic systems with any desired further substitution, and connected to G2 and O by a monovalent bond in each case;
G5 and G6 are each identical or different units connected to P by a monovalent bond and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

In a particular embodiment of formula 2:
G1 is an at least disubstituted 1,2-, 1,3- or 1,4-phenyl radical;
G2 is a C1-alkyl radical with tertiary or quaternary substitution;
G3 and G4 are the same and are each an at least monosubstituted aromatic radical and selected from the group of aromatics, heteroaromatics, fused aromatics systems or fused heteroaromatic systems with any desired further substitution;
G5 and G6 are the same and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-alkyl, N-aryl, N-heteroaryl, N-cycloalkyl, N-silyl.

In a particularly preferable embodiment of formula 2:

G1 is a 1,3-disubstituted phenyl radical;
G2 is a C1-alkyl radical substituted with hydrogen or methyl;
G3 and G4 are the same and selected from the group tert-butylphenoxy, methoxy-tert-butylphenoxy or di-tert-butylphenoxy;
G5 and G6 are the same and selected from the group tert-butylphenoxy, methoxy-tert-butylphenoxy, naphthoxy, di-tert-butylphenoxy, methyl-tert-butylphenoxy or pyrrole.

The organic phosphorus compounds claimed in these embodiments—also referred to as tetraphenol ligands or tetraphenol-substituted bisphosphites—are hereinbelow further disclosed and characterized in the preparation examples according to the invention.

For clarity, the tetraphenol ligands claimed are referred to as TP1 to TP7 in the preparation examples according to the invention. The structures belonging to the claimed tetraphenol ligands are likewise disclosed in scheme 1 in the preparation examples according to the invention.

Further embodiments of formula 2 according to the invention are recited by way of example in the following structure which is designated TP:

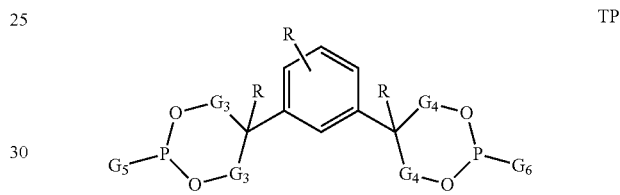

TP

Where, according to the TP formula, G3 and G4 are the same or different and each represents an at least monosubstituted cyclic structure, for example

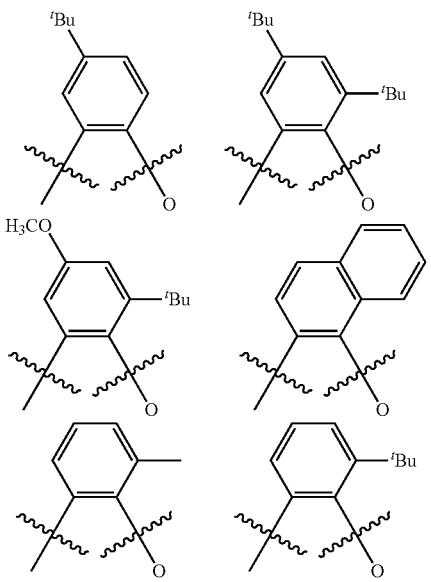

Where G5 and G6 are each identical or different units connected to P by a monovalent bond and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl; for example

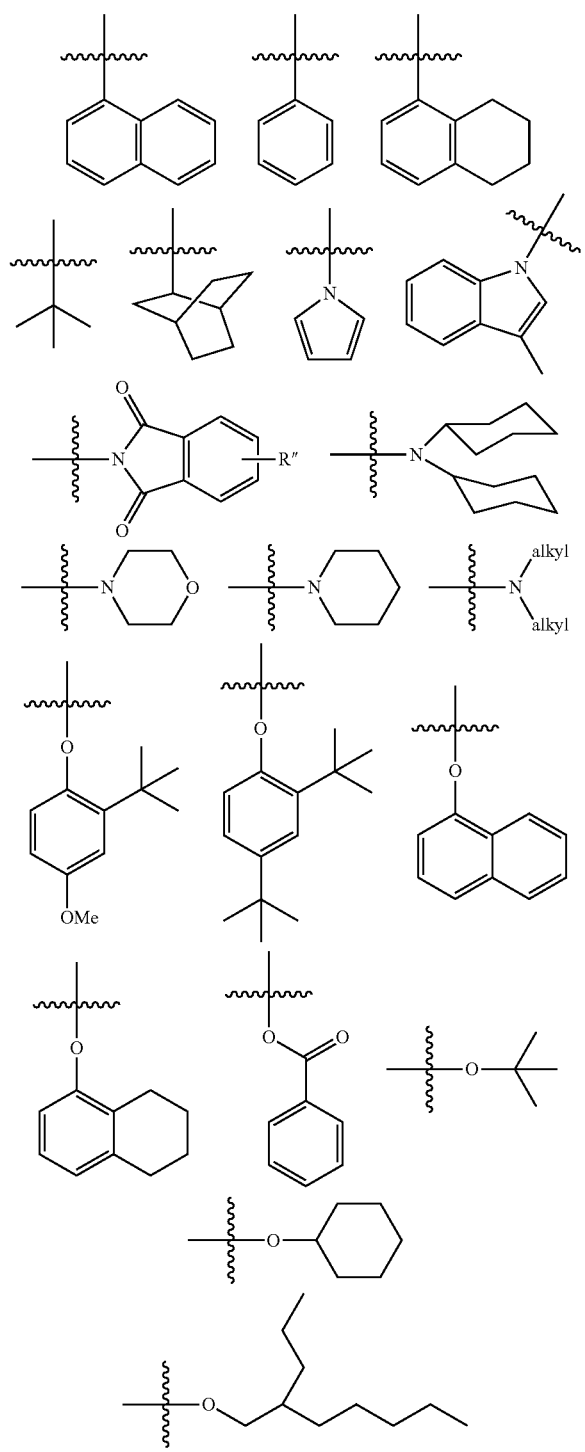

and R is for example hydrogen, methyl, trifluoromethyl or phenyl; and

R' is for example represented by the following radicals:

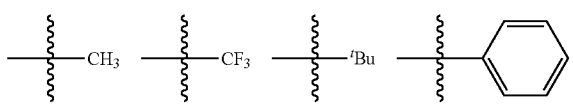

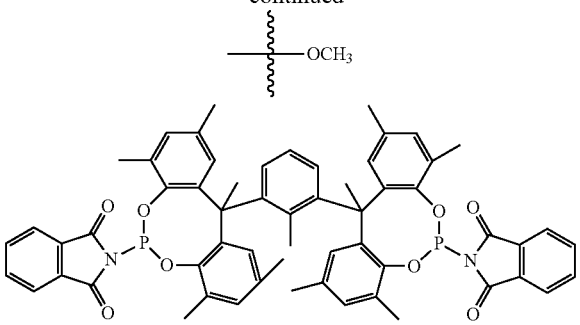

The present invention also provides organic phosphorus compounds of formula 3

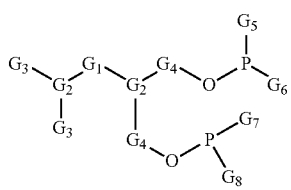

(3)

where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 is in each case substituted by an OH group and is an at least disubstituted cyclic structure selected from the group of aromatics, heteroaromatics, fused aromatics systems or fused heteroaromatic systems with any desired further substitution, and connected to G2 by a monovalent bond in each case;
G4 is an at least monosubstituted cyclic structure selected from the group of aromatics, heteroaromatics, fused aromatics systems or fused heteroaromatic systems with any desired further substitution, and connected to G2 and O by a monovalent bond in each case;
G5, G6, G7 and G8 are each identical or different units or G5 paired with G6 and G7 paired with G8 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The invention further provides organic phosphorus compounds of formula 4

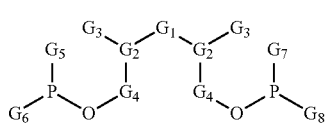

(4)

where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 is in each case substituted by an OH group and is an at least disubstituted cyclic structure selected from the group of aromatics, heteroaromatics, fused aromatics systems or fused heteroaromatic systems with any desired further substitution, and connected to G2 by a monovalent bond in each case;
G4 is an at least monosubstituted cyclic structure selected from the group of aromatics, heteroaromatics, fused aromatics systems or fused heteroaromatic systems with any desired further substitution, and connected to G2 and O by a monovalent bond in each case;
G5, G6, G7 and G8 are each identical or different units or G5 paired with G6 and G7 paired with G8 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The present invention also provides organic phosphorus compounds of formula 5

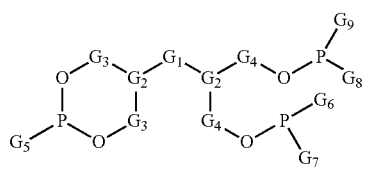

5 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 and G4 are the same or different and are each an at least disubstituted cyclic structure selected from the group of aromatics, heteroaromatics, fused aromatics systems or fused heteroaromatic systems with any desired further substitution, and connected to G2 and O by a monovalent bond in each case;
G5, G6, G7, G8 and G9 are each identical or different units or G6 paired with G7 and G8 paired with G9 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The invention further provides organic phosphorus compounds of formula 6

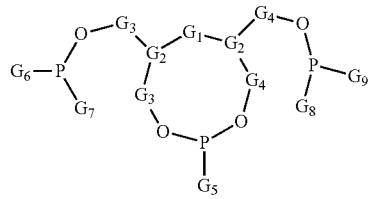

6 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 and G4 are the same or different and are each an at least disubstituted cyclic structure selected from the group of aromatics, heteroaromatics, fused aromatics systems or fused heteroaromatic systems with any desired further substitution, and connected to G2 and O by a monovalent bond in each case;
G5, G6, G7, G8 and G9 are each identical or different units or G6 paired with G7 and G8 paired with G9 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The present invention also provides organic phosphorus compounds of formula 7

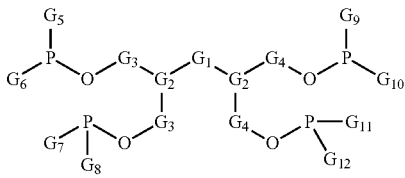

7 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 and G4 are the same or different and are each an at least disubstituted cyclic structure selected from the group of aromatics, heteroaromatics, fused aromatics systems or fused heteroaromatic systems with any desired further substitution, and connected to G2 and O by a monovalent bond in each case;

G5, G6, G7, G8, G9, G10, G11 and G12 are each identical or different units or G5 paired with G6 and G7 paired with G8, G9 paired with G10 and G11 paired with G12 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

In a particular embodiment according to formula 7:

G1 is a 1,3-disubstituted phenyl radical;

G2 is a C1-alkyl radical substituted with hydrogen, methyl, ethyl, isopropyl, isobutyl, trifluoromethyl or aryl;

G3 and G4 are the same and selected from the group tert-butylphenoxy or di-tert-butyl-phenoxy;

G5, G6, G7, G8, G9, G10, G11 and G12 are each identical or different units or G5 paired with G6 and G7 paired with G8, G9 paired with G10 and G11 paired with G12 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

Exemplary structures of this embodiment are:

39

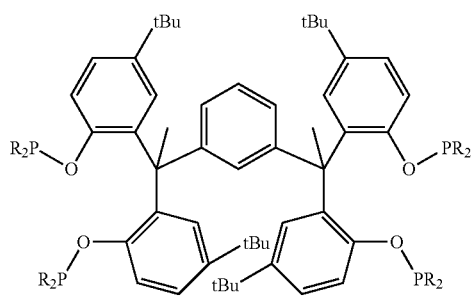

Where PR$_2$ in formula 39 exhibits for example the following substitution:

40

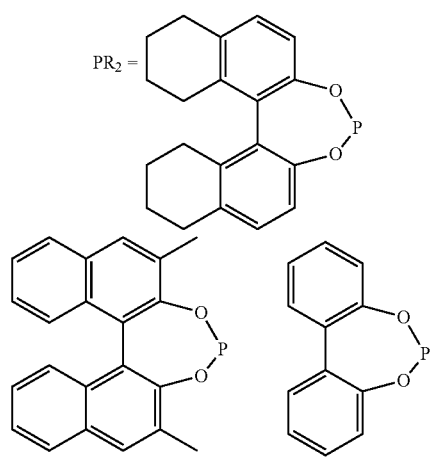

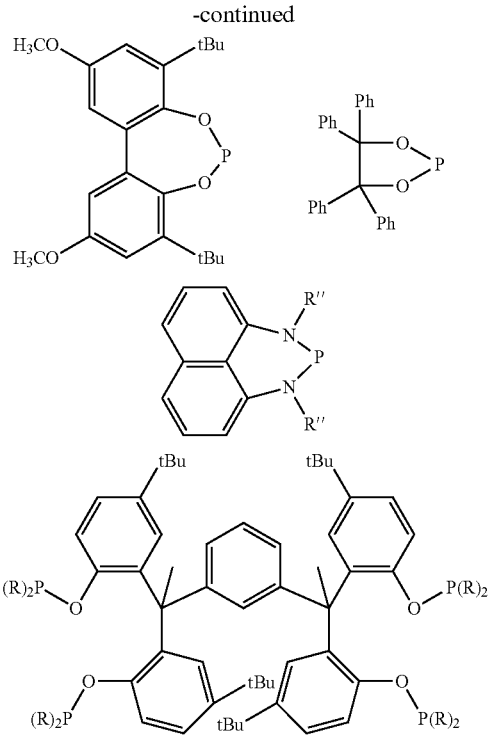

Where R in formula 40 represents for example the following moieties:

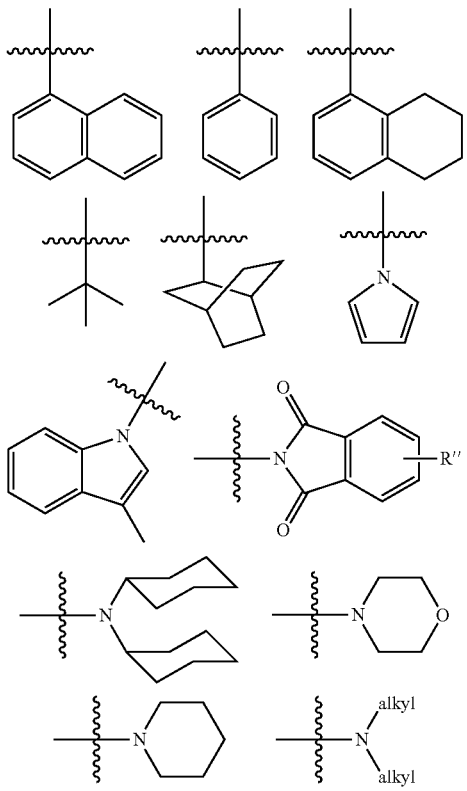

-continued

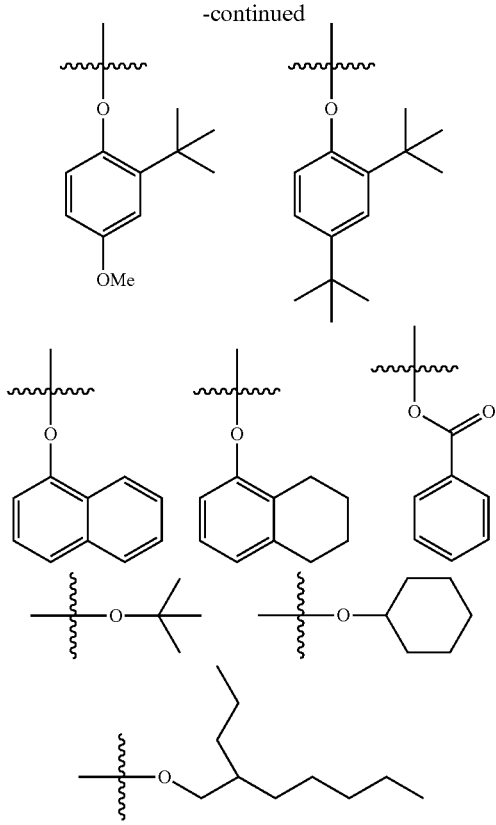

The representative of formula 40 where R=2,4-di-tert-bu-tylphenoxy is an embodiment claimed according to the invention and constitutes a tetraphenol-based tetraphosphite, this embodiment being further disclosed, under the TP8 formula, in the preparation examples according to the invention.

The invention further provides organic phosphorus compounds of formula 8

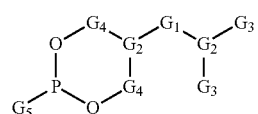

8 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 is in each case substituted by an OH group and is an at least disubstituted cyclic structure selected from the group of aromatics, heteroaromatics, fused aromatics systems or fused heteroaromatic systems with any desired further substitution, and connected to G2 by a monovalent bond;
G4 is an at least monosubstituted cyclic structure selected from the group of aromatics, heteroaromatics, fused aromatics systems or fused heteroaromatic systems with any desired further substitution, and connected to G2 and O by a monovalent bond in each case;
G5, G6, G7, G8, G9 and G10 are each identical or different units or G5 paired with G6, G7 paired with G8 and G9 paired with G10 are each covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The present invention also provides organic phosphorus compounds of formula 9

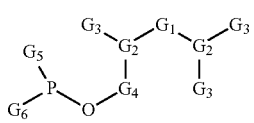

9 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;
G3 is in each case substituted by an OH group and is an at least disubstituted cyclic structure selected from the group of aromatics, heteroaromatics, fused aromatics systems or fused heteroaromatic systems with any desired further substitution, and connected to G2 by a monovalent bond;
G4 is an at least monosubstituted cyclic structure selected from the group of aromatics, heteroaromatics, fused aromatics systems or fused heteroaromatic systems with any desired further substitution, and connected to G2 and O by a monovalent bond in each case;
G5 is a unit linked to P by a monovalent bond and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The invention further provides organic phosphorus compounds of formula 10

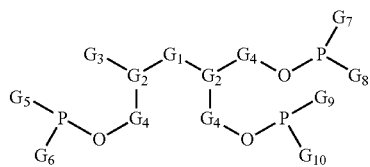

10 where:
O in each occurrence is an oxygen atom,
P in each occurrence is a phosphorus atom,
G1 is an at least disubstituted cyclic structure selected from the group of aromatics, heteroaromatics, fused aromatics systems or fused heteroaromatic systems with any desired further substitution, and connected to G2 by a monovalent bond in each case;
G2 is an alkyl radical and is connected to G1, G3 and/or G4 by a monovalent bond in each case;

G3 is in each case substituted by an OH group and is an at least disubstituted cyclic structure selected from the group of aromatics, heteroaromatics, fused aromatics systems or fused heteroaromatic systems with any desired further substitution, and connected to G2 by a monovalent bond;

G4 is an at least monosubstituted cyclic structure selected from the group of aromatics, heteroaromatics, fused aromatics systems or fused heteroaromatic systems with any desired further substitution, and connected to G2 and O by a monovalent bond in each case;

G5 and G6 are each identical or different units or G5 paired with G6 are covalently linked units connected to P by monovalent bonds and selected from the group O-alkyl, O-aryl, O-acyl, O-heteroaryl, O-cycloalkyl, O-silyl, acyl, alkyl, aryl, heteroaryl, cycloalkyl, perfluoroalkyl, N-acyl, N-alkyl, N-aryl, N-heteroaryl, N-cycloalkyl, N-silyl.

The invention also provides metal complexes containing a metal of group 4, 5, 6, 7, 8, 9 or 10 of the periodic table and one or more organic phosphorus compounds which are recited as TP1, TP2, TP3, TP4 or TP5 in the preparation examples according to the invention.

In a particular embodiment, the metal complexes according to the invention are characterized in that the metal is rhodium, palladium, nickel, platinum, cobalt or ruthenium.

In a further embodiment, at least one of the organic phosphorus compounds referred to as TP1, TP2, TP3, TP4 or TP5 in the preparation examples according to the invention and/or a metal complex based on rhodium, palladium, nickel, platinum, cobalt or ruthenium finds use in catalysis.

In a further embodiment, at least one of the organic phosphorus compounds referred to as TP1, TP2, TP3, TP4 or TP5 in the preparation examples according to the invention and/or a metal complex based on rhodium, palladium, nickel, platinum, cobalt or ruthenium finds advantageous use in homogeneous catalysis.

In a very particular embodiment, at least one of the organic phosphorus compounds referred to as TP1, TP2, TP3, TP4 or TP5 in the preparation examples according to the invention and/or a metal complex based on rhodium, palladium, nickel, platinum, cobalt or ruthenium finds use in a process for hydroformylation of olefin-containing mixtures.

The metal complexes claimed are further disclosed and characterized in the preparation examples according to the invention.

The invention also provides a process for hydrocyanation of pentenenitrile-containing streams using a catalytically active composition, characterized in that the catalytically active composition contains an organic phosphorus compound which is referred to as TP1, TP2, TP3, TP4 or TP5 in the preparation examples according to the invention. Further details of the disclosure are found in the process examples according to the invention.

A particular embodiment of the hydrocyanation process according to the invention is characterized in that the hydrocyanation is effected by foreclosing any isomerization to branched nitriles. Further details of the disclosure are found in the process examples according to the invention.

The invention further provides a process for hydrocyanation of butadiene-containing streams using a catalytically active composition, characterized in that the catalytically active composition contains an organic phosphorus compound which is referred to as TP2 in the preparation examples according to the invention.

A particular embodiment of the process for hydrocyanation of butadiene-containing streams characterized in that butadiene is hydrocyanated to linear pentenenitriles with an n/iso selectivity of more than 99%. Further details of the disclosure are found in the process examples according to the invention.

The invention also provides a process for hydroformylation of unsaturated hydrocarbon mixtures using a catalytically active composition containing a transition metal of groups 8 to 10, characterized in that the catalytically active composition includes an organic phosphorus compound which is referred to as TP1, TP2, TP3, TP4 or TP5 in the preparation examples according to the invention.

A particular embodiment of the process for hydroformylating unsaturated hydrocarbon mixtures which is in accordance with the invention is characterized in that the catalytically active composition contains an organic phosphorus compound referred to as TP1, TP2, TP3, TP4 or TP5 in the preparation examples according to the invention and rhodium. Further details of the disclosure are found in the process examples according to the invention.

A further embodiment of the process for hydroformylating unsaturated hydrocarbon mixtures which is in accordance with the present invention is characterized in that a stream containing olefins having at least 4 to 20 carbon atoms is used as unsaturated hydrocarbon mixture. A preferable embodiment utilizes the following streams as unsaturated hydrocarbon mixture:

raffinate I in commercially available composition;

raffinate III in commercially available composition, containing a remainder of C4-alkanes, linear C4-alkenes and also isobutene and C5-alkanes;

so-called crude butane containing C4-alkanes, linear C4-alkenes and C5-alkanes;

so-called dibutene containing at least 98% by mass of C8-olefins, based on the total amount of C8-olefins, selected from the group of dimethylhexenes, methylheptenes and also n-octenes;

so-called tributenes containing a mixture of at least 98% by mass of C11- and C12-olefins, based on the total amount of C11- and C12-olefins.

Further details of the disclosure are found in the process examples according to the invention.

The invention further provides a process for hydroaminoalkylation of unsaturated hydrocarbon mixtures using a catalytically active composition containing a transition metal of groups 8 to 10, characterized in that the catalytically active composition includes an organic phosphorus compound referred to as TP6 in the preparation examples according to the invention.

A particular embodiment of the hydroaminoalkylation process according to the invention is characterized in that the catalytically active composition contains an organic phosphorus compound referred to as TP6 in the preparation examples according to the invention and rhodium.

A further embodiment of the hydroaminoalkylation process according to the invention is characterized in that the chemoselectivity concerning the product amine is above 90% and the formation of byproducts is below 10%. Further details of the disclosure are found in the process examples according to the invention.

The invention also provides a process for hydrogenation of unsaturated hydrocarbon mixtures using a catalytically active composition containing a transition metal of groups 8 to 10, characterized in that the catalytically active composition includes an organic phosphorus compound referred to as TP1 in the preparation examples according to the invention. Further details of the disclosure are found in the process examples according to the invention.

The invention further provides a process for hydrosilylation of carbonyl compounds using a catalytically active composition containing a transition metal of groups 8 to 10, characterized in that the catalytically active composition includes an organic phosphorus compound referred to as TP3 in the preparation examples according to the invention. Further details of the disclosure are found in the process examples according to the invention.

EXAMPLES

The examples which follow illustrate the invention.

Preparation Examples According to the Invention

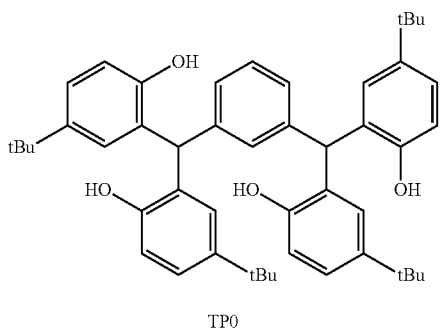

TP0

Scheme 1: Tetraphenol ligands TP1-7 and their $^{31}P\{^{1}H\}$ NMR shifts.

| Ligand | TP1 | TP2 | TP3 | TP4 | TP5 | TP6 | TP7 |
|---|---|---|---|---|---|---|---|
| R | 4-tBu-phenoxy | 2-tBu-4-OMe-phenoxy | naphthyloxy | 2,4-di-tBu-phenoxy | 2,6-di-tBu-methylphenoxy | pyrrolyl | 2,4-di-tBu-phenoxy |
| R' | H | H | H | H | H | H | CH₃ |
| $^{31}P$ NMR δ | 122.1 | 122.6 | 119, 129 | 122.1 | 172.6 | 122.8 | 105.5 |

Synthesis Examples

Preparation of Tetraphenol Core Structure TP0:
4,4',4'',4'''-tetra-t-butyl-2,2',2'',2'''-(phenylenemethanediyl) tetraphenol

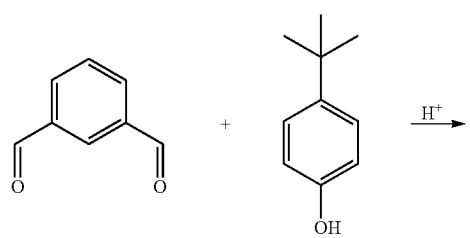

The tetraphenol core structure TP0 was prepared according to a modified literature method [C. Gruettner, V. Boehmer, R. Assmus, S. Scherf, *J. Chem. Soc., Perkin Trans.* 1 1995, 93-94]:

A mixture of 4-tert-butylphenol (72 g, 0.48 mol) and isophthalaldehyde (8.1 g, 0.06 mol) is heated with stirring until a homogeneous melt has formed (100-110° C.). HCl (8 ml) is then metered in followed by stirring for a further 6 hours. Excess phenol is removed by steam distillation and the residue is recrystallized from acetone. Yield: 0.043 mol, 29.9 g, 71.5%.

$^{1}$H NMR (CDCl$_{3}$): δ 7.28-7.24 (m, 1H), 7.11-7.05 (m, 7H), 6.93 (d, J=2.4 Hz, 4H), 6.71 (d, J=8.4 Hz, 4H), 5.83 (s, 2H), 5.24 (bs, 4H, —OH), 1.13 (s, 36H). $^{13}$C NMR (CDCl$_{3}$): δ 150.93, 143.65, 141.99, 128.11, 127.28, 124.64, 115.74, 77.66, 77.02, 76.39, 45.14, 34.04, 31.40. Elemental analysis for C$_{48}$H$_{58}$O$_{4}$*2(CH$_{3}$)CO: Calculated/observed: % C, 79.57 (79.74), % H, 8.66 (8.43).

Preparation of Tetraphenol Core Structure TP'0
4,4',4'',4'''-tetra-t-butyl-2,2',2'',2'''-(phenylenemethyl-methanediyl)tetraphenol

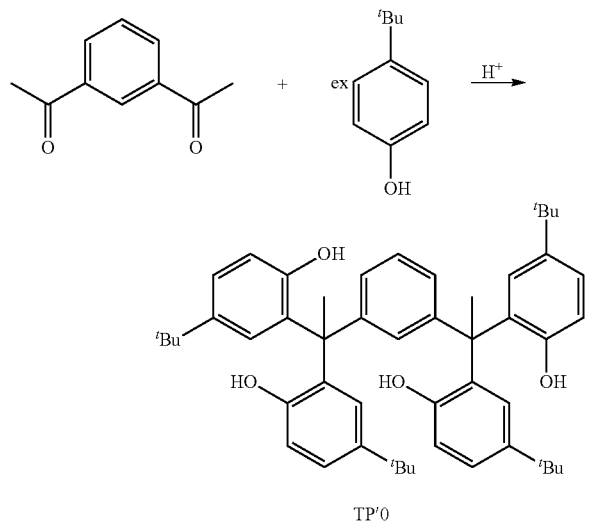

TP'0

A mixture of 4-tert-butylphenol (138.7 g, 0.924 mol) and 1,3-diacetylbenzene (10.0 g, 0.0616 mol) is heated with stirring until a homogeneous melt is formed (140° C.). Thereafter, methanesulfonic acid (5.3 g, 0.0553 mol, 3.59 ml) is added and the reaction mixture is heated for 24 h. Excess phenol is removed by steam distillation and the residue is recrystallized from acetone. Yield of crude product: 46.28 mmol, 33.6 g, 75.1%. $^1$H NMR (CDCl$_3$): δ 7.44 (bs, 1H), 7.17 (dd, J=8.4, 2.4 Hz, 2H), 7.10-7.08 (m, 1H), 6.99-6.96 (m, 8H), 6.94 (d, J=2.4 Hz, 4H), 4.58 (bs, 4H, —OH), 1.91 (s, 6H), 1.16 (s, 36H).

Preparation of Tetraphenol Core Structure TP''0
6,6',6'',6'''-tetra-o-methyl-2,2',2'',2'''-(phenylen-emethanediyl)tetraphenol

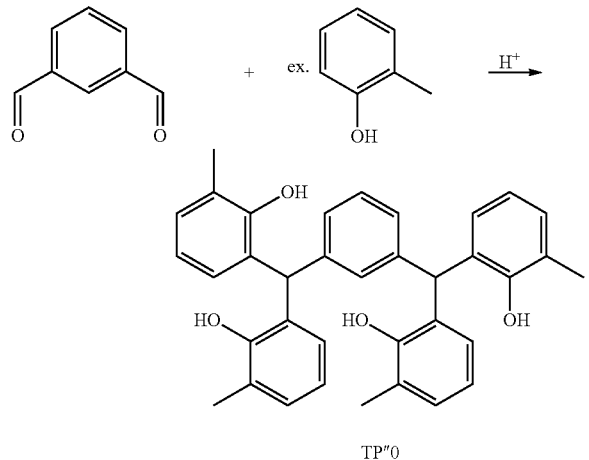

TP''0

A mixture of o-cresol (52 g, 0.48 mol) and isophthalaldehyde (8.1 g, 0.06 mol) is heated with stirring until a homogeneous melt has formed (100-110° C.). HCl (8 ml) is then metered in and stirring is continued for a further 6 hours. Thereafter, excess phenol is removed by steam distillation and the crude product is analyzed by NMR spectroscopy. Target product purities of 90-95% were detected. Yield crude product (still contains o-cresol): 34.3 g, 96%. $^1$H NMR (CDCl$_3$): δ 7.16-7.13 (m, 1H), 7.00-6.88 (m, 4H), 6.84-6.74 (m, 8H), 6.70-6.69 (m, 1H), 6.65-6.61 (m, 2H), 5.28 (s, 2H), 4.91 (bs, 4H, —OH), 2.16 (s, 12H).

Preparation of Bisphosphite TP1

A solution of PCl$_3$ (0.6 mg, 6.5 mmol) in 35 ml of THF is admixed with tetraphenol core structure TP0 (2.1 g, 3 mmol) and Et$_3$N (5.4 ml, 36 mmol) at −10° C. by dropwise addition, and stirred for 30 min. Thereafter, 4-tert-butylphenol (6.05 mmol) dissolved in 10 ml of THF is added dropwise at −10° C. The solution is stirred at room temperature for an hour, the salt is filtered off through a layer of basic alumina (4 cm) and the filtrate is concentrated to dryness. Yield: 0.96 mmol, 1.01 g, 32%. $^1$H NMR (CDCl$_3$): δ 7.38-7.35 (m, 2H), 7.33-7.30 (m, 2H), 7.24 (d, J=2.9 Hz, 4H), 7.20-7.06 (m, 8H), 6.99 (dd, J=8.5, 0.9, 4H), 6.85-6.77 (m, 4H), 5.77 (s, 2H), 1.08 (s, 54H). $^{13}$C NMR (CD$_2$Cl$_2$): 150.08, 149.96, 147.34, 146.99, 143.45, 134.50, 128.58, 128.14, 127.94, 126.48, 126.37, 126.24, 126.14, 125.47, 125.31, 123.40, 120.31, 120.22, 120.16, 53.24, 34.32, 34.25, 31.83, 31.14. $^{31}$P NMR (CD$_2$Cl$_2$): δ 122.08. Elemental analysis for C$_{68}$H$_{80}$O$_6$P$_2$: calculated (observed): % C, 77.39 (77.33), % H, 7.64 (7.45).

Preparation of Bisphosphite TP2

Method similar to TP1, but 4-hydroxy-3-tert-butylanisole is added instead of 4-tert-butylphenol.

Yield: 0.84 mmol, 937 mg, 28%. $^1$H NMR (CDCl$_3$): δ 7.47-7.43 (m, 2H), 7.33 (s, 4H), 7.11-6.96 (m, 12H), 6.48-6.43 (m, 4H), 5.72 (s, 2H), 3.29 (s, 6H), 1.36 (s, 18H), 1.09 (s, 36H). $^{13}$C NMR (CD$_2$Cl$_2$): 155.57, 147.77, 146.54, 146.43, 144.89, 144.60, 141.82, 141.78, 133.76, 128.87, 128.74, 128.06, 127.80, 127.02, 126.48, 125.29, 125.14, 122.93, 120.41, 120.11, 114.32, 109.99, 55.57, 45.57, 34.67, 34.16, 31.11, 29.1462. $^{31}$P NMR (CDCl$_3$): δ 122.61.

Preparation of Bisphosphite TP3

Method similar to TP1, but 1-naphthol is added instead of 4-tert-butylphenol. Yield: 2.1 mmol, 2.2 g, 70.4%. $^1$H NMR (CDCl$_3$): δ 8.18 (d, J=8 Hz, 2H), 7.82 (d, J=8 Hz, 2H), 7.68-7.60 (m, 2H), 7.46-7.42 (m, 3H), 7.42-7.47 (m, 8H), 7.28 (s, 4H), 7.09-7.05 (m, 3H), 6.95-6.85 (m, 6H), 5.60 (s, 2H), 1.13 (s, 36H). $^{13}$C NMR (CD$_2$Cl$_2$): 147.71, 147.63, 146.44, 146.32, 134.87, 134.59, 128.72, 127.64, 127.52, 127.44, 127.35, 126.62, 126.51, 126.25, 126.08, 125.84, 125.73, 125.58, 125.26, 124.24, 123.82, 123.12, 122.54, 122.28, 115.10, 114.87, 95.04, 34.32, 31.43. $^{31}$P NMR (CDCl$_3$): δ 131.38. Elemental analysis for C$_{68}$H$_{68}$O$_6$P$_2$: calculated (observed): %C 78.29 (77.93), %H 6.57 (6.23).

Preparation of Bisphosphite TP4

Method similar to TP1, but 2,4-di-tert-butylphenol is added instead of 4-tert-butylphenol. Yield: 2.4 mmol, 2.8 g, 80.7%. $^1$H NMR (CDCl$_3$): δ 7.30 (d, J=2.5 Hz, 2H), 7.28-7.20 (m, 8H), 7.08-7.01 (m, 6H), 6.78-6.74 (m, 2H), 6.61 (dt, J=4.9 Hz, 0.8 Hz, 4H), 5.83 (s, 2H), 1.42 (s, 18H), 1.29 (s, 54H). $^{13}$C NMR (CD$_2$Cl$_2$): 151.58, 149.08, 147.85, 147.49, 146.54, 146.08, 145.75, 138.95, 133.85, 128.79, 126.45, 125.34, 124.92, 124.53, 124.03, 123.50, 123.02, 119.89, 119.07, 118.84, 118.70, 110.41, 45.76, 34.90, 34.82, 34.33, 34.22, 31.18, 29.95. $^{31}$P NMR (CD$_2$Cl$_2$): δ 122.12. Elemental analysis for C$_{76}$H$_{96}$O$_6$P$_2$*CH$_2$Cl$_2$: calculated (observed): %C 73.84 (74.32), %H 7.89 (8.19).

Preparation of Bisphosphite TP5

Method similar to TP1, but 2-tert-butyl-6-methylphenol is added instead of 4-tert-butylphenol. Yield: 2.3 mmol, 2.5 g, 77.5%. $^1$H NMR (CDCl$_3$): δ 7.30 (d, J=2.5 Hz, 2H), 7.26-7.20 (m, 6H), 7.13-7.03 (m, 8H), 7.01-6.90 (m, 4H), 6.77-6.65 (m, 2H), 6.22 (s, 2H), 2.52 (s, 6H), 1.49 (s, 54H). $^{13}$C NMR (CD$_2$Cl$_2$): 149.44, 149.35, 147.82, 147.53, 146.92, 146.88, 145.97, 145.80, 139.54, 139.30, 139.21, 138.97, 128.70, 127.58, 124.68, 124.57, 124.40, 123.94, 123.16, 120.48, 115.12, 114.88, 35.08, 32.53, 31.27, 30.00, 25.78. $^{31}$P NMR (CD$_2$Cl$_2$): δ 172.59. Elemental analysis for C$_{70}$H$_{84}$O$_6$P$_2$*CH$_2$Cl$_2$: calculated (observed): %C 72.99 (72.32), %H 7.42 (7.57).

Preparation of Bisphosphoramidite TP6

Method similar to TP1, but pyrrole is added instead of 4-tert-butylphenol. $^{31}$P NMR (CD$_2$Cl$_2$): δ 122.77.

Preparation of Bisphosphite TP7

Tetraphenol core structure TP'0 (0.3 g, 0.41 mmol) and Et$_3$N (0.2 ml, 1.4 mmol) are added dropwise at −10° C. to a solution of PCl$_3$ (0.1 mg, 1.13 mmol) in 5 ml of THF and the reaction solution is stirred for 30 min. Thereafter, 2,4-di-tert-butylphenol (0.17 g, 0.825 mmol) dissolved in 1 ml of THF is added dropwise at −10° C., followed by stirring at room temperature for 1 h. The salt is filtered off through a layer of basic alumina (4 cm) and the filtrate is concentrated to dryness. Yield: 0.14 mmol, 0.165 g, 33.3%. $^1$H NMR (CDCl$_3$): δ 7.44 (bs, 1H), 7.17 (dd, J=8.4, 2.4 Hz , 2H), 7.10-7.08 (m, 1H), 6.99-6.96 (m, 12H), 6.93 (d, J=2.4 Hz, 6H), 1.91 (s, 6H), 1.42 (s, 9H), 1.29 (s, 9H), 1.16 (s, 54H). $^{31}$P NMR (CD$_2$Cl$_2$): δ 105.53.

Preparation of Tetraphosphite TP8

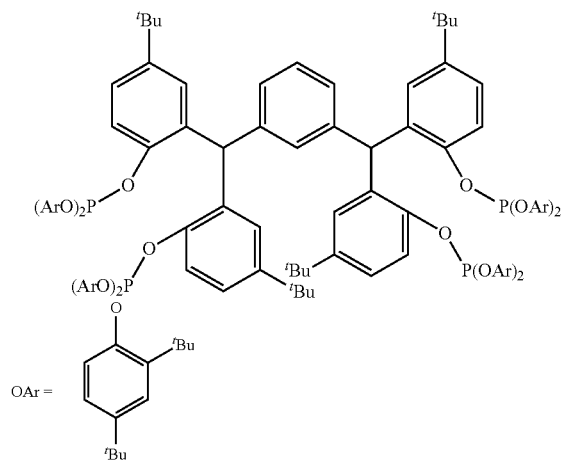

To a solution of PCl$_S$ (0.3 ml, 3.25 mmol) in 30 ml of THF are added in succession at −10° C. 2,4-di-tert-butylphenol (1.355 g, 6.5 mmol) and Et$_3$N (2.4 ml, 16.0 mmol) by dropwise addition, followed by stirring for 30 min. Thereafter, a solution of tetraphenol core structure TP0 (0.57 g, 0.812 mmol) in 5 ml of THF is added dropwise at −10° C. followed by stirring at room temperature for 1 h. The salt is filtered off through a layer of basic alumina (4 cm) and the filtrate is concentrated to dryness. $^{31}$P NMR (THF): δ 128.0.

Synthesis of Platinum Complex (TP1)PtCl$_2$

Pt(cod)Cl$_2$ (35 mg, 94 μmol) and TP1 (121 mg, 113 μmol) were stirred in 4 ml of CH$_2$Cl$_2$/CH$_3$CN (3/2 mixture) at room temperature for 1 h. After one week at −30° C., crystals suitable for x-ray crystal structure analysis were obtained. Yield: 86.8 mg, 65.7 μmol, 62%. $^1$H NMR (CD$_2$Cl$_2$): δ 7.45 (dd, J=8.7 Hz, 2.0 Hz, 4H), 7.40-7.00 (m, 16H), 6.79-6.81 (m, 4H), 5.56 (s, 2H) 1.41 (s, 18H), 1.32 (s, 36H). $^{13}$C NMR (CD$_2$Cl$_2$): δ 154.29, 153.15, 152.15 149.82, 143.32, 138.11, 133.67, 132.97, 132.62, 130.91, 130.68, 130.18, 125.78, 123.63, 61.36, 38.77, 35.46. $^{31}$P NMR (CD$_2$Cl$_2$/CH$_3$CN=3/2): δ 45.57 (J$_{Pt-P}$=6091.46 Hz).

Synthesis of Nickel Complexes (L)Ni(CO)$_2$ [C. J. Cobley and P. G. Pringle, *Inorg. Chim. Acta* 1997, 265, 107-115]

10 mg (0.036 mmol) of Ni(cod)$_2$ and 1 mol equivalent of TP ligand (0.036 mmol) were dissolved in 2 mL of toluene. CO was bubbled through the bright yellow solution for 30 min, which then turned colorless. It was concentrated in vacuo to dryness and the remaining solid was analyzed by ATR-IR spectroscopy:

| Ligand | A$_1$ (cm$^{-1}$) | B$_1$ (cm$^{-1}$) |
|---|---|---|
| TP1 | 2043 | 1995 |
| TP2 | 2040 | 1987 |
| TP3 | 2043 | 1991 |
| TP4 | 2041 | 1990 |
| TP5 | 2043 | 2002[a] |

[a]several species present

Synthesis of (TP2)Ni(cod)

A solution of TP2 (22.0 mg, 0.018 mmol) in 1 mL of benzene-d6 was added to Ni(cod)$_2$ (5.0 mg, 0.018 mmol) and stirred in a Schlenk vessel for 30 min. $^1$H NMR (500 MHz, C$_6$D$_6$) δ (ppm): 8.75 (d, J=8.5 Hz), 7.75 (s), 7.48 (d, J=8.5 Hz), 7.23-7.19 (m), 7.12 (s), 7.07 (s), 7.03 (s), 6.99 (s), 6.44 (d, J=8.5 Hz), 5.56 (s), 5.27 (s), 3.51 (s), 3.35 (s), 2.11 (s), 1.69 (s), 1.58-1.54 (m), 1.48 (s), 1.42-1.04 (m), 0.99 (s). $^{31}$P NMR (202 MHz, CDCl$_3$) δ (ppm): 124.6 (s).

Synthesis of (TP2)Ni(2M3BN)—ZnCl$_2$

A solution of TP2 (89.0 mg, 0.079 mmol) in 3 mL of toluene-d8 was added to Ni(cod)$_2$ (22.0 mg, 0.079 mmol) and stirred in a Schlenk vessel for 5 min. 2M3BN (10 μL, 1 eq.) was added by means of an Eppendorf pipette as well as ZnCl$_2$ as Lewis acid (22.0 mg, 1 equiv.). The solution was stirred for 30 min, a sample (800 μL) was taken for NMR analysis and the remaining solution was concentrated to dryness in vacuo. The reddish orange powder was analyzed by IR spectroscopy. IR (cm$^{-1}$) ]: 3061 [C=(C—H)]; 2150 (CN). $^1$H NMR (400 MHz, C$_6$D$_6$) δ (ppm): 8.26 (br s), 7.59-6.94 (m), 6.47 (d, J=8.4 Hz), 6.21-6.10 (m), 5.08 (m), 4.78 (br s), 4.42 (br s), 4.16 (br s), 3.95 (br s), 3.83 (br s), 3.64 (br s), 3.44-3.40 (m), 3.37 (s), 3.36 (d, J=2 Hz), 3.34-3.30 (m), 3.30 (d, J=3 Hz), 3.28 (s), 2.92 (br s), 2.62 (br s), 1.59-0.82 (m), 0.64 (d, J=6.8 Hz), 0.25 (s). $^{13}$C NMR (100.6 MHz, C$_6$D$_6$) δ (ppm): 156.46, 153.72, 148.49, 148.27, 146.70, 137.10, 129.15, 128.88, 126.55, 125.29, 124.12, 116.64, 115.94, 114.02, 110.54, 70.49, 69.44, 66.56, 55.71, 54.87, 35.54, 34.26, 33.94, 30.95, 29.95, 29.82, 29.31, 28.91, 27.98, 14.94, 1.01. $^{31}$P NMR (400 MHz, C$_6$D$_6$) δ (ppm): 124.6 (bs). Maldi-Tof: 1114.39 (TP2), 1172.36 (TP2Ni), 1227.40 (TP2Ni(2M3BN)—CN).

Process Examples According to the Invention

Hydrocyanation

Nickel-catalyzed hydrocyanation of 3-pentenenitrile (3PN): To Ni(cod)$_2$ (5.0 mg, 0.018 mmol) is added the ligand solution (0.018 mmol of TP ligand in 2 mL of solvent). Thereafter, 3-pentenenitrile (300 μL, 170 eq.) is added by means of an Eppendorf pipette as well as 50 μL of n-decane as internal standard and the Lewis acid (1 eq.). The solution obtained is transferred to a 15 ml Schlenk vessel. Acetonecyanohydrin (400 μL, 250 eq.) is then added by means of an Eppendorf pipette and the Schlenk vessel is heated until 90° C. in an oil bath. The solution is stirred for 4 h, then cooled down to 0° C. and stripped with an argon stream for 1 min to remove HCN traces. The samples were determined by gas chromatography using n-decane as internal standard. All the reactions were carried out twice, the duplicates being observed to vary by ±2% and ±1% in conversion and selectivity respectively.

TABLE 1

Hydrocyanation of 3PN (3-pentenenitrile) with TP1-TP5 ligands

| Input | Ligand | Conversion[a] % | 2PN[b] % | 4PN[b] % | Yield of DN[c] % | ADN/MGD |
|---|---|---|---|---|---|---|
| 1 | TP1 | 24 | 10 | / | 14 | 83/17 |
| 2 | TP2 | 39 | 0 | 19 | 20 | 96/4 |
| 3 | TP3 | 15 | 1 | 7 | 7 | 75/25 |
| 4 | TP4 | 14 | 1 | 1 | 12 | 59/41 |
| 5 | TP5 | 15 | 1 | 8 | 6 | 68/32 |

Conditions: 0.018 mmol of Ni(cod)$_2$, Ni:L:Zn:LA:ACH = 1:1:1:170: excess, acetonecyanohydrin (ACH) as HCN source, T = 90° C., 2 mL of toluene, t = 4 h.
[a]Determined by gas chromatography with n-decane as internal standard. Conversions are based on amount of unconverted substrates [mmol].
[b]Yield of 2-pentenenitrile and 4-pentenenitrile respectively;
[c]Yield of dinitriles: adiponitrile (ADN) + methylglutaronitrile (MGD).

TABLE 2

Hydrocyanation of 3PN with TP2 ligand

| Input | Lewis acid | Conversion[a] % | Other nitriles[b] (%) [2PN-4PN-2M2BN] | Yield of DN[c] (%) [ADN/MGD] |
|---|---|---|---|---|
| 6 | ZnCl$_2$ (1 eq) | 41 | [4-5-0] | 32 [88/12] |
| 7 | ZnCl$_2$ (2 eq) | 40 | [4-2-0] | 34 [88/12] |
| 8 | ZnCl$_2$ (5 eq) | 14 | [1-1-0] | 12 [85/15] |
| 9 | ZnCl$_2$ (3 eq) | 53 | [3-11-0] | 38 [85/15] |
| 10[d] | ZnCl$_2$ (3 eq) | 29 | [3-9-0] | 20 [87/13] |
| 11 | AlCl$_3$ (1 eq) | 1 | [0.2-0.4-0] | 0.1 [100/0] |
| 12[e] | ZnCl$_2$ (3 eq) | 43 | [3-17-1] | 22 [82/18] |

Conditions: 0.018 mmol of Ni(cod)$_2$, Ni:L:Zn:LA:ACH = 1:1:1:170: excess, acetonecyanohydrin (ACH) as HCN source, T = 90° C., 2 mL of THF, t = 4 h, TP2 as ligand.
[a]Determined by gas chromatography with n-decane as internal standard. Conversions are based on amount of unconverted substrates [mmol].
[b]Yield of 2-pentenenitrile, 4-pentenenitrile and 2-methyl-2-butenenitrile;
[c]Yield of dinitriles: adiponitrile + methylglutaronitrile;
[d]T = 110° C.;
[e]BIPPP as benchmark ligand with the following structure:

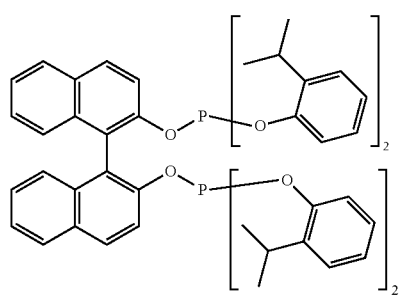

Binaphthyl Phosphite Ligand (BIPPP) as Benchmark Ligand

TABLE 3

Hydrocyanation of 4PN in THF with TP2 ligand

| Input | Conversion[a] % | 2PN[b] % | 3PN[b] % | Yield of DN[c] % | ADN/MGD |
|---|---|---|---|---|---|
| 1 | 98.5 | 3.6 | 53 | 42 | 89/11 |

Conditions: 0.018 mmol of Ni(cod)$_2$, Ni:L:Zn:LA:ACH = 1:1:1:170: excess, acetonecyanohydrin (ACH) as HCN source, T = 90° C., 2 mL of THF, t = 4 h, TP2 as ligand.
[a]Determined by gas chromatography with n-decane as internal standard. Conversions are based on amount of unconverted substrates [mmol].
[b]Yield of 2-pentenenitrile and 3-pentenenitrile respectively;
[c]Yield of dinitriles: adiponitrile (ADN) + methylglutaronitrile (MGD).

TABLE 4

Hydrocyanation of butadiene in dioxane with various ligands

| Input | Ligand | Conversion[a] % | 3PN % | 2M3BN % | Other nitriles % |
|---|---|---|---|---|---|
| 1 | TP2 | 1.6 | 100 | / | / |
| 2 | Phosphite[b] | 78.3 | 63.2 | 34.1 | 2.7 |
| 3 | Sixantphos | 80.2 | 53.1 | 41.5 | 5.4 |

Conditions: 0.018 mmol of Ni(cod)$_2$, Ni:L:Zn:LA:ACH = 1:1:1:125: excess, acetonecyanohydrin (ACH) as HCN source, T = 90° C., 2 mL of dioxane, t = 5 h.
[a]Determined by gas chromatography with n-decane as internal standard. Conversions are based on amount of unconverted substrates [mmol];
[b]Phosphite = [1,1']-binaphthenyl 2,2'-bis[di-(2-isopropylphenyl) phosphite General prescription for isomerization experiments: Ni(cod)$_2$ (5.0 mg, 0.018 mmol) is admixed with the ligand solution (0.018 mmol of TP ligand in 2 mL of solvent) by stirring under inert gas for 5 min. 2-Methyl-3-butenenitrile, 2M3BN, (200 μL, 100 eq.) is added by means of an Eppendorf pipette as well as 50 μL of n-decane as internal standard and ZnCl$_2$ as Lewis acid (5.0 mg, 1 eq.). The Schlenk vessel is oil bath heated to 90° C. and samples are taken at regular intervals for GC analysis. Selectivity is defined as 3PN/(Σ nitriles).

Hydroformylation

Reactions with the model substrates 1-octene, trans-2-octene, n-octene mixture, dibutene, isobutene and cis-2-butene are shown by way of example. Rhodium concentration was 40 and 200 ppm.

The results of hydroformylating 1-octene and trans-2-octene are hereinbelow shown by way of example. These reactions were carried out in an AMTEC SPR16 parallel reactor. Rh(acac)(CO)$_2$ (3.7 mg, 14.4 μmol) and 4 mol equivalents of ligand (57.6 μmol) were dissolved in 5 ml of toluene and the solution was transferred to the argon-filled reaction vessel. This was heated to 80° C. and pressurized with 20 bar of synthesis gas. After 2 h preformation time, the substrate mixture (18 mmol of 1-octene and 6 mmol of n-decane as internal standard) was added. The reaction solution was stirred at 80° C. and 20 bar synthesis gas for 24 h.

TABLE 5

Hydroformylation of 1-octene

| Ligand | Conversion (%) | Linear/branched | Aldol product (%) | TOF[a] |
|---|---|---|---|---|
| TP1 | 98 | 4.6 | 0.1 | 800 |
| TP2 | 99 | 2.7 | 0.1 | 1400 |
| TP3 | 99 | 12.3 | 0.3 | 460 |

TABLE 5-continued

Hydroformylation of 1-octene

| Ligand | Conversion (%) | Linear/branched | Aldol product (%) | TOF[a] |
|---|---|---|---|---|
| TP4 | 99 | 7.4 | 0.5 | 300 |
| TP5 | 99 | 2.7 | 0.1 | 55 |

Conditions: Rh:L:LA = 1:4:1250, 80° C., 20 bar CO/$H_2$ (1:1), toluene, [Rh] = 1.92 mM, Rh precursor = Rh(acac)(CO)$_2$, $V_{tot}$ = 8 mL, t = 24 h;
[a]TOF determination at 20% conversion.

TABLE 6

Hydroformylation of trans-2-octene

| Ligand | Time (h) | Pressure (bar) | Temperature (° C.) | Conversion (%) | Linear/branched ratio | TOF[a] |
|---|---|---|---|---|---|---|
| TP2 | 18 | 20 | 80 | 17 | 0.18 | 11 |
| TP3 | 18 | 20 | 80 | 11 | 0.67 | 8 |
| TP2 | 25 | 10 | 140 | 67 | 1.27 | 56 |
| TP3 | 25 | 10 | 140 | 39 | 1.92 | 68 |
| TP3[b] | 35 | 10 | 140 | 45 | 1.55 | 10 |

Conditions: Rh:L:LA = 1:4:1250, toluene, [Rh] = 1.92 mM, Rh precursor = Rh(acac)(CO)$_2$;
[a]TOF determination at 20% conversion;
[b]Rh:L = 1:20

C4-olefin dimerization dibutene (C8-olefin mixture, linear and branched isomers) were hydroformylated with TP1 ligand without solvent:

TABLE 7

Hydroformylation of dibutene (C8-olefin mixture, linear and branched isomers)

| Ligand | Olefin | Pressure (bar) | Temperature (° C.) | Conversion (%) | Selectivity[a] (%) |
|---|---|---|---|---|---|
| TP1 | Dibutene | 60 | 115 | 49 | 99 |
| TP1 | Dibutene | 260[b] | 135 | 84 | 99+ |

Conditions: Rh:L = 1:4; 50 bar CO/$H_2$ (1:1), 6 h, [Rh] = 40 ppm, solvent-free, 1 kg of di-n-butene;
[a]chemoselectivity = aldehyde/conversion;
[b][Rh] = 20 ppm.

The following examples relating to hydroformylation of C4-olefins (table 8) and C8-olefins (table 9) were carried out in 100 ml Parr autoclaves equipped with a pressure regulator to keep the constant pressure, a gas flow meter and a blade stirrer. The autoclave was filled with all the hereinbelow specified compounds, but not with the olefin mixture to be hydroformylated, under argon. After replacing the argon atmosphere by purging with synthesis gas (CO/$H_2$ 1:1), the reaction mixture was heated to the particular temperature mentioned under agitation (1000 rpm) and under synthesis gas pressure, and thereafter adjusted to the exact target pressure of 20 bar. Thereafter, the olefin mixture to be hydroformylated was added. The synthesis gas pressure was kept constant throughout the entire reaction time, via a pressure regulator. The reaction time was 720 min for each of the hydroformylation tests, during which samples were removed from the autoclave for GC analysis. The reaction mixture was subsequently cooled down to room temperature, the autoclave was depressurized and purged with argon.

TABLE 8

Hydroformylation of C4-olefins

| Ligand | Olefin | Pressure (bar) | Temperature (° C.) | Conversion (%) | n-Selectivity[a] (%) | k (min$^{-1}$) |
|---|---|---|---|---|---|---|
| TP1 | cis-2-Butene | 20 | 120 | 99 | 60 | 0.0089 |
| TP2 | cis-2-Butene | 20 | 120 | 97 | 38 | 0.0047 |
| TP4 | cis-2-Butene | 20 | 120 | 98 | 40 | 0.0063 |
| TP1 | Isobutene | 20 | 120 | 91 | — | 0.0043 |
| TP2 | Isobutene | 20 | 120 | 54 | — | 0.0011 |
| TP4 | Isobutene | 20 | 120 | 60 | — | 0.0014 |

Conditions: Rh:L = 1:4; 6 g C4-olefin, 120° C., 20 bar CO/$H_2$ (1:1), t = 720 min, toluene, [Rh] = 40 ppm, Rh precursor = Rh(acac)(CO)$_2$;
[a]n-selectivity = pentanal/total aldehydes, at time t = 720 min

TABLE 9

Hydroformylation of 1-octene and n-octene mixture

| Ligand | Olefin | Pressure (bar) | Temperature (° C.) | Conversion (%) | n-Selectivity[a] (%) | K[b] (min$^{-1}$) |
|---|---|---|---|---|---|---|
| TP1 | 1-Octene | 20 | 100 | 99 | 78 | 0.0009 |
| TP2 | 1-Octene | 20 | 100 | 99+ | 71 | 0.0242 |
| TP3 | 1-Octene | 20 | 100 | 99 | 95 | 0.0056 |
| TP4 | 1-Octene | 20 | 100 | 99+ | 73 | 0.0035 |
| TP5 | 1-Octene | 20 | 100 | 99 | 95 | 0.0063 |
| TP1 | n-Octenes | 20 | 100 | 59 | 47 | 0.0019 |
| TP2 | n-Octenes | 20 | 120 | 58 | 28 | 0.0012 |
| TP3 | n-Octenes | 20 | 120 | 17 | 70 | 0.0004 |
| TP4 | n-Octenes | 20 | 120 | 44 | 31 | 0.0008 |
| TP5 | n-Octenes | 20 | 120 | 16 | 64 | 0.0004 |

Conditions: Rh:L = 1:4; 10 g C8-olefin, 20 bar CO/$H_2$ (1:1), t = 720 min, toluene, [Rh] = 40 ppm, Rh precursor = Rh(acac)(CO)$_2$;
[a]n-selectivity = nonanal/total aldehyde, at time t = 720 min;
[b]k (min$^{-1}$) after isomerization, not the initial rate.

Hydroaminomethylation
Hydroaminomethylation of 1-octene with TP6

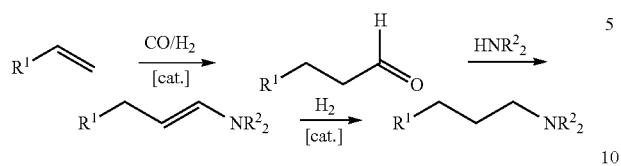

This cascade reaction, consisting of hydroformylation and reductive amination, was carried out using [Rh(cod)$_2$]BF$_4$ as precursor. The reaction was carried out in a toluene/methanol mixture at 110° C. and 36 bar of CO/H$_2$ (1:2) and a stirrer speed of 800 rpm. Full conversion was reached after 2 h, activity is remarkably high. This reaction is fast and very chemo-selective.

TABLE 10

Hydroaminomethylation of 1-octene and piperidine with ligand TP6

| Input | t (min) | Conversion (%) | Alkene isomers (%) | Linear/branched[a] | Amine sel. (%) |
|---|---|---|---|---|---|
| 1 | 26 | 92 | 2 | 10.4 | 48 |
| 2 | 51 | 98 | 1 | 8.5 | 69 |
| 3 | 96 | 99+ | — | 2.2 | 93 |
| 4 | 124 | 99+ | — | 2.0 | 95 |

[a]based on amines obtained.

Hydrogenation
Hydrogenation of Dimethyl Itaconate with TP1

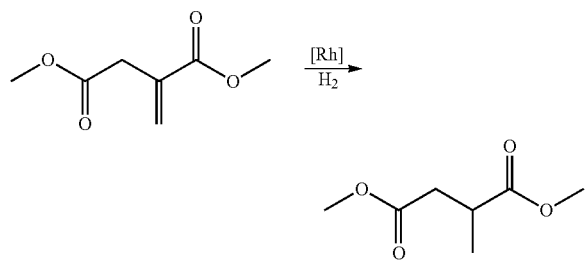

[Rh(cod)$_2$]BF$_4$ (4 mg, 9.85 μmol) was dissolved in 2 mL of CH$_2$Cl$_2$ and added to TP1 (10 μmol). The yellow catalyst solution was stirred at room temperature for 30 min and then metered into a solution of dimethyl itaconate (300 mg, 2 mmol) in 3 mL of CH$_2$Cl$_2$. This solution was stirred at room temperature under 1 bar H$_2$ atmosphere for 24 h. Substrate conversion was 100% (GC).

Hydrosilylation
Hydrosilylation of Acetophenone with TP3

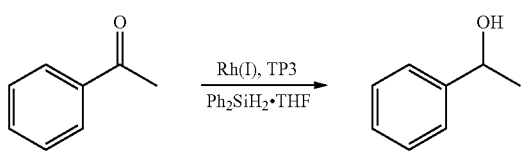

In a 50 mL Schlenk vessel, 0.36 mL of acetophenone and 0.58 mL of diphenylsilane are added dropwise, via a syringe, to a solution of [Rh(nbd)$_2$]BF$_4$ (11.5 mg, 4.75 μmol) and TP3 (150 mg, 14.25 μmol) in 3 ml of THF, and the solution obtained is stirred under argon at room temperature for 18 h. Thereafter, 6 ml of HCl (10% in H$_2$O) were added and the solution is extracted twice with 6 ml of diethyl ether each time. Conversion was 46% (GC).

The invention claimed is:

1. An organic phosphorus compound of formula 2:

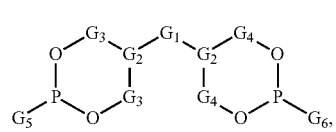

wherein:
G1 is an at least disubstituted 1,2-, 1,3-, or 1,4-phenyl radical, and is connected to G2 by a monovalent bond in each case;
G2 is a C1-alkyl radical comprising a tertiary or quaternary substitution;
G3 and G4 are the same and are each an at least monosubstituted aromatic radical selected from the group consisting of an aromatic, a heteroaromatic, a fused aromatic system, and a fused heteroaromatic system; and
G5 and G6 are the same and selected from the group consisting of O-alkyl, O-aryl, O-acyl, O-heteroaryl, O-cycloalkyl, O-silyl, acyl, alkyl, aryl, heteroaryl, cycloalkyl, perfluoroalkyl, N-alkyl, N-aryl, N-heteroaryl, N-cycloalkyl, and N-silyl.

2. The compound of claim 1, wherein:
G1 is a 1,3-disubstituted phenyl radical;
G2 is a C1-alkyl radical substituted with hydrogen or methyl;
G3 and G4 are the same and selected from the group consisting of tert-butylphenoxy, methoxy-tert-butylphenoxy, and di-tert-butylphenoxy;
G5 and G6 are the same and selected from the group consisting of tert-butylphenoxy, methoxy-tert-butylphenoxy, naphthoxy, di-tert-butylphenoxy, methyl-tert-butylphenoxy, and pyrrole.

3. A process for hydroformylation of an unsaturated hydrocarbon mixture, the process comprising:
contacting an unsaturated hydrocarbon with a catalytically active composition comprising (i) a transition metal of groups 8 to 10 and (ii) an organic phosphorus compound of claim 1.

4. A process for hydroformylation of an unsaturated hydrocarbon mixture, the process comprising:
contacting an unsaturated hydrocarbon with a catalytically active composition comprising an organic phosphorus compound of claim 2 and rhodium.

5. The process of claim 3, wherein the unsaturated hydrocarbon mixture is a stream containing olefins comprising at least 4 to 20 carbon atoms.

6. A metal complex, comprising:
a metal of group 4, 5, 6, 7, 8, 9, or 10 of the periodic table; and
an organic phosphorus compound of claim 1.

7. The metal complex of claim 6, wherein the metal is rhodium, palladium, nickel, platinum, cobalt, or ruthenium.

8. A process of making a catalyst, the process comprising combining an organic phosphorus compound of claim 1 with a metal of group 4, 5, 6, 7, 8, 9, or 10, thereby producing a catalyst.

9. The process of claim 8, wherein the catalyst produced is homogeneous.

10. A process for hydroformylation of an unsaturated hydrocarbon mixture, the process comprising:
   contacting an unsaturated hydrocarbon with a catalytically active composition comprising an organic phosphorus compound of claim 2 and rhodium.

11. The process of claim 10, wherein the unsaturated hydrocarbon mixture is a stream containing olefins comprising at least 4 to 20 carbon atoms.

12. A metal complex, comprising:
   a metal of group 4, 5, 6, 7, 8, 9, or 10 of the periodic table; and
   an organic phosphorus compound of claim 2.

* * * * *